United States Patent [19]

Henner et al.

[11] Patent Number: 5,198,337
[45] Date of Patent: Mar. 30, 1993

[54] ASSAY FOR GENE DELETION OF GST-1 IN HUMAN SAMPLES BASED ON THE POLYMERASE CHAIN REACTION

[75] Inventors: William D. Henner; Kenine E. Comstock; Barbara J. S. Sanderson; Virginia J. Claflin, all of Portland, Oreg.

[73] Assignee: State of Oregon, Portland, Oreg.

[21] Appl. No.: 509,054

[22] Filed: Apr. 13, 1990

[51] Int. Cl.$^5$ .............................................. C12Q 1/68
[52] U.S. Cl. .......................................... 435/6; 435/91; 435/172.3; 436/501; 436/811; 536/24.33; 935/9; 935/17; 935/78; 935/88
[58] Field of Search .......................... 435/6, 91, 172.3; 436/501, 811; 536/27; 935/9, 17, 78, 88

[56] References Cited

U.S. PATENT DOCUMENTS 4,683,202  7/1987  Mullis .................................... 435/91

OTHER PUBLICATIONS

Seidegard et al. (1988) Proc. Natl. Acad. Sci. (USA) vol. 85, pp. 7293-7297.
Porschen et al., 1983, Cell Tissue Kinet. 16: 549-556.
Erlich, *Basic Methodology*, in PCR Technology, Erlich (ed.), Stockton Press, New York, 1989, pp. 1-5.
Saiki, *The Design and Optimization of PCR*, in PCR Technology, Erlich (ed.), Stockton Press, New York, 1989, pp. 7-16.
Gibbs et al., 1989, Curr. Commun. Mol. Biol., Polymerase Chain Reaction, Erlich, Gibbs & Kazazian, eds., Cold Spring Harbor Press, pp. 83-91.
Mullis, *The Polymerase Chain Reaction: Why It Works*, 1989, in Curr. Commun. Mol. Biol., Polymerase Chain Reaction, Erlich, Gibbs & Kazazian, eds., Cold Spring Harbor Press, pp. 237-243.
Noonan et al., 1990, Proc. Natl. Acad. Sci. USA 87: 7160-7164.
Baker et al., 1990, Growth Dev. Aging 54: 85-93.
Alanen et al., 1989, Cytometry 10: 417-425.
Noonan & Roninson, *Quantitative Estimation of MDR1 mRNA Levels by Polymerase Chain Reaction*, in Molecular and Cellular Biology of Multidrug Resistance in Tumor Cells, Roninson, ed. (Plenum, New York), 1991, pp. 319-333.
Chumakov et al., 1991, Proc. Natl. Acad. Sci. USA 88: 199-203.
Patel et al., 1986, Mol. Cell. Biol. 6: 393-403.
Koenig et al, 1987, Cell 50: 509-517.
Xu et al., 1989, Terat. Carcin. Mutagen. 9: 177-187.
Saiki, et al., (1988, Science 239: 487-491).
Kim and Smithies (1988, Nucleic Acids Res. 16: 8887-8903).
Boehm (1989, Clin. Chem. 35: 1843-1848).
Lynas et al., (1989, J. Gen. Virol. 70: 2345-55).
Losekoot et al., (1989, Hum. Genet. 83: 75-78).
Boerwinkle et al., (1989, Nucleic Acids Res. 17: 4003).
Wrischnik et al., (1987, Nucleic Acid Res. 15: 529-542).
Seidegard et al., (1985, Carcinogenesis 6: 1211-1216).
Seidegard et al., (1986, Carcinogenesis 7: 751-753).
Lai et al., (1988, J. Biol. Chem. 263: 11389-11395).

*Primary Examiner*—Margaret Moskowitz
*Assistant Examiner*—Ardin H. Marschel
*Attorney, Agent, or Firm*—Allegretti & Witcoff, Ltd.

[57] ABSTRACT

Methods for the detection of GST-1 gene deletion in human blood or tissue samples. The polymerase chain reaction is used to identify the presence or absence of the GST-1 gene in human clinical samples as a means of assessing susceptibility to neoplasia or toxicity upon chemical exposure. The method may also be used on human tumor samples to assess the possibility of resistance to certain chemotherapeutic agents.

2 Claims, No Drawings

ASSAY FOR GENE DELETION OF GST-1 IN HUMAN SAMPLES BASED ON THE POLYMERASE CHAIN REACTION

This invention was made with government support under CA 35767 awarded by the National Institutes of Health. The government has certain rights in the invention.

BACKGROUND OF THE INVENTION

1. Field of the Invention

The invention relates to assays for deletion of human genes which may be involved in neoplastic disorders. More particularly, the invention relates to the efficient detection of the deficiency of the human glutathione transferase (GST) isoenzyme GST-mu through the analysis of human blood or tissue samples in the clinical laboratory, as a means of predicting susceptibility to human neoplasia, including lung cancer. The invention further relates to means for predicting resistance of tumors to certain anticancer drug therapy as well as to the identification of individuals who may be at abnormally high risk of toxic effects upon exposure to chemicals which are detoxified by the GST-mu protein.

2. Summary of the Related Art

Mullis et al., U.S. Pat. No. 4,683,202 discloses the polymerase chain reaction (PCR).

Saiki et al., (1988, Science 239: 487–491) discloses the use of the thermostable Taq polymerase in PCR.

Kim and Smithies (1988, Nucleic Acids Res. 16: 8887–8903) discloses conditions for carrying out PCR on cell lysates in a recombinant fragment assay.

Boehm (1989 Clin. Chem. 35: 1843–1848) discusses the use of PCR for prenatal testing for inherited disorders.

Lynas et al., (1989, J. Gen. Virol. 70: 2345–55) discloses the use of PCR in the detection of viral gene expression.

Losekoot et al., (1989, Hum. Genet. 83: 75–78) discloses detection of a franeshift insertion mutation in a thalassemia gene, using PCR.

Boerwinkle et al. (1989, Nucleic Acids Res. 17: 4003) discusses the use of PCR to type an insertion/deletion polymorphism in a human apolipoprotein B gene.

Shvarts et al., (1989, Biorg. Khim. 15: 556–559) discloses characterization of the molecular nature of a deletion in a beta-globin gene, using PCR.

Xu et al., (1989, Teratogenesis Carcinog. Mutagen. 9: 177–187) discloses the use of PCR for deletion screening at the hgprt locus in cultured Chinese hamster cells.

Wrischnik et al., (1987, Nucleic Acid Res. 15: 529–542) discloses the identification of length mutations in human mitochondrial DNA by direct sequencing of PCR-amplified DNA.

While the related art discloses a variety of uses for PCR in the identification of mutations, there is no teaching of the use of PCR to detect large deletions in genes contained in highly necrotic tissues. Additionally, the existing art does not provide a means for effectively carrying out PCR at the GST-1 locus, and the existing technology for detecting the absence of GST-mu protein (MUKIT, Medlabs, Dublin, Ireland) relies on immunological methods to detect protein, and is thus unsuited to the assay of tissue samples, particularly highly necrotic tissue samples, such as those found in tumors.

There is a need for a better assay for GST-1 presence and expression, because of the significant role of the GST-mu isozyme in human physiology.

Seidegard et. al., (1985, Carcinogenesis 6: 1211–1216) teaches that the human glutathione transferase GST-mu is frequently deficient in individuals, and that such deficiency can result in altered metabolic activity toward certain toxic chemicals.

Seidegard et al. (1988, Proc. Natl. Acad. Sci. USA 85: 7293–7297) teaches that GST-mu deficiency is due to homozygous deletion of the GST-1 gene; and further provides DNA sequence information for the human cDNA for GST-mu.

Seidegard et al., (1986, Carcinogenesis 7: 751–753) teaches that GST-mu deficiency is associated with an increased risk for lung cancer.

Lai et al., (1988, J. Biol. Chem. 263: 11389–11395) discloses sequence information for a rat genomic clone related to the human GST-1 gene.

BRIEF SUMMARY OF THE INVENTION

The invention relates to the efficient detection of gene deletion in human clinical samples which is associated with increased susceptibility to neoplasia or to toxicity upon chemical exposure. The invention further relates to means for identifying the capacity for existing tumors to resist certain chemotherapeutic regimens. More particularly, the invention provides a convenient and effective assay, based on the polymerase chain reaction (PCR), for the detection of glutathione transferase (GST) deficiency as a result of homozygous deletion of the GST-1 gene. Using synthetic DNA primers homologous to the 5' region of exon 4 and the 3' region of exon 5 of the GST-1 gene, the assay of the invention can detect homozygous deletion of the GST-1 gene in patient's blood or tissue samples. Unlike existing technologies which rely on immunologic methods, the assay of the invention is suitable for analyzing tissue samples, including highly necrotic tumor tissue samples from which GST-mu protein cannot be accurately determined.

DETAILED DESCRIPTION OF THE SPECIFIC EMBODIMENTS

The human glutathione transferase (GST) isoenzyme GST-mu is frequently deficient (31–66%) in human lymphocytes or liver samples. The absence of GST-mu has been reported to be a marker for increased risk of lung cancer and increased levels of GST-mu may be linked to drug resistance. The absence of GST-mu has been ascribed to homozygous deletion of the gene for GST-mu (GST-1) in deficient individuals. We have developed a PCR-based assay to determine the presence or absence of the GST-1 gene in samples of human DNA. Using primers homologous to the 5' region of exon 4 and the 3' region of exon 5 of the GST-1 gene and DNA from individuals whose lymphocytes contain GST-mu on Western blotting, a ~273 bp. DNA fragment is produced consisting of exon 4, intron 4 and exon 5 of GST-1. This assay confirms that homozygous GST-1 gene deletion is the predominant mechanism for GST-mu deficiency in the human population and provides a convenient alternative to Southern blotting for this determination. Likewise, Western blotting and this PCR assay have been used to determine that GST-1 gene was present in all (7/7) of GST-mu Western blot-positive breast carcinomas but not in (0/10) GST-mu negative breast carcinomas. The GST-mu status of human breast carcinomas is determined by the presence or absence of the GST-1 gene and appears to simply reflect the heredity of the individual developing the cancer.

In a first aspect, the invention provides an assay for the presence or absence of the GST-1 gene in human blood, tissue or tumor samples. Due to the relative stability of DNA and the sensitivity of the assay, which requires only 1 microgram of DNA, the technique is applicable to highly necrotic tumor tissue samples. Thus, the invention is superior to Southern blotting for this purpose, since it is more convenient, requires much less starting material, and does not require the high molecular weight DNA required for efficient Southern blotting, but commonly absent from necrotic tissue samples. Similarly, the invention is superior for this purpose to existing immunologic methods for the detection of GST-mu protein, since the available system (MUKIT, Medlabs, Dublin, Ireland) is not suitable for analyzing tissue samples, and is particularly unsuited for analysis of highly necrotic tumor tissue, from which GST-mu protein cannot be accurately determined.

The present invention satisfies this aspect in part by providing a selection of primers which efficiently amplifies a portion of the GST-1 gene. Suitable primers include any primers which allow a specific amplification of GST-1 sequences from about $10^6$ to about $10^7$-fold. In a preferred embodiment, Primer 1 hybridizes to the 5' region of exon 4 of GST-1 and comprises the sequence:

5'-CTGCCCTACTTGATTGATGGG-3' while Primer 2 hybridizes to the opposite DNA strand at the 3' region of exon 5 of GST-1 and comprises the sequence:

5'-CTGGATTGTAGCAGATCATGC-3'.

To carry out the assay of the invention it is necessary to have a source of cellular DNA. In one embodiment of the present invention, white blood cells may be isolated from whole blood by standard procedures. DNA can then be isolated from the isolated white blood cells and used in the polymerase chain reaction. About 1 microgram of DNA is sufficient. In an alternative embodiment, isolated white blood cells may themselves be used for the assay as cell lysates without prior isolation of the DNA. For these purposes, it is preferred that from about $10^6$ to about $10^7$ white blood cells be used. In yet another embodiment cellular DNA may be obtained by extraction of tissue or tumor biopsy material. About 1 microgram of DNA is necessary for carrying out the assay.

Whichever of the above sources of cellular DNA is used, the assay is carried out by mixing the DNA source with primers 1 and 2, or with other suitable primers, in the presence of all four deoxynucleotide triphosphates and a DNA polymerase, preferably a heat stable polymerase such as the Taq polymerase. Amplification is achieved by subjecting the mixture to alternating cycles of temperatures which allow first denaturation, then annealing, then DNA synthesis. When a thermostable enzyme is used, there is no need to add enzymes between cycles. Typically, enough DNA is produced by the amplification process to be visualized on a DNA gel after from about 30 to about 40 cycles. When primers 1 and 2 above are used in the reaction, a 273 base pair DNA fragment corresponding to GST-1 exons 4 and 5 and intron 4 is produced.

In another aspect, the invention provides a method for screening individuals for susceptibility to certain types of neoplasia, including lung cancer. Since GST-mu deficiency is fairly frequent in the population and has been related to an increased risk of lung cancer, the assay of the invention provides a convenient means for testing individuals for such increased risk, by obtaining blood or tissue samples and carrying out the assay as described.

In another aspect, the invention provides a method for assessing whether neoplastic growth in a particular individual is likely to be effectively treated by certain chemotherapeutic agents, since increased GST-mu expression is linked to anticancer drug resistance. Tumor tissue samples may be used to extract cellular DNA by standard procedures, which DNA is then used to carry out the assay as described.

In another aspect, the invention provides a method for screening individuals for an increased risk of toxic effects upon becoming exposed to certain chemicals which are detoxified in part by GST-mu protein. Such screening will conveniently result from the same assay performed to assess increased susceptibility to lung cancer.

Further preferred embodiments will become evident from the following examples and the claims.

EXAMPLE 1

Detection of GST-1 Gene Presence or Absence In Human Breast Carcinoma Following Isolation of DNA Samples of human breast carcinomas that had been stored at $-20°$ C. were pulverized and DNA prepared by a standard procedure (Treco, D. A. In Current Protocols in Molecular Biology, Greene Publishing Associates and Wiley-Interscience, New York, pp. 221-222, 1987) including removal of RNA by Rnase digestion. DNA was quantitated by absorbance at 260 nm. Polymerase chain reactions included 1 microgram of target DNA, oligonucleotide primers (5'-CTGCCCTACTT-GATTGATGGG-3' and 5'-CTGGATTGTAG-CAGATCATGC-3') at 1.0 micromolar each, buffer (final concentrations 50 Mm KCl, 10 Mm Tris-HCl (pH 8.3) 1.5 mM MgCl$_2$, 0.01% (w/v) gelatin), dATP, dCTP, dGTP and TTP (200 micromolar each) and 2.5 units of AmpliTaq TM DNA polymerase (US Biochemical, Cleveland, Ohio), in a final volume of 100 microliters. Reactions were incubated in a Programmable Cyclic Reactor TM (Ericomp Inc., San Diego, Calif.) with a cycle of 2 min. at 94° C., 1 min. at 55° C. and 1.5 min. at 72° C. for a total of 35 cycles. Ten microliters of the reaction mixtures were loaded into the well of a 2.1% agarose gel containing 0.5 micrograms/microliters of ethidium bromide and DNA size markers were loaded into adjacent wells. The gel was subjected to 75 volts for 2 hours. The position of the polymerase chain reaction products and size marker DNAs were recorded by photography under ultraviolet light illumination. Polymerase chain reactions with DNA derived from breast carcinomas that contain mu class glutathione transferase by Western blotting contained a 273 base pair product. All but one of those derived from breast cancers that did not contain mu class glutathione transferase by Western blotting did not produce the 273 base pair product.

EXAMPLE 2

Detection of GST-1 Gene Presence or Absence in Human Lymphocytes Following Isolation of DNA Human blood samples were obtained by venipuncture and lymphocytes isolated by centrifugation on Ficoll/Hypaque gradients. DNA was prepared as in Example 1. Polymerase chain reactions and detection of product were as described in Example 1.

EXAMPLE 3

Detection of GST-1 Gene Presence or Absence In Human Lymphocyte Lysates

Human blood samples were obtained by venipuncture and lymphocytes isolated by centrifugation on Ficoll/Hypaque gradients. $6 \times 10^6$ cells were pelleted by centrifugation, resuspended in 2 ml of distilled water and incubated at 37° C. for 5 min. An aliquot (3.3 microliters equivalent to $10^4$ cells) was transferred to the polymerase chain reaction. The remainder of the reaction was performed as in Examples 1 and 2, except that target DNA was omitted.

What is claimed is:

1. A method for detecting a homozygous deletion of at least exon 4 through exon 5 in a GST-1 gene in human blood or tissue samples comprising the steps of:
   (a) isolating cellular DNA from the human blood or tissue sample;
   (b) providing a mixture comprising a DNA polymerase, deoxynucleotide triphosphates, the isolated cellular DNA, and a pair of primers comprising DNA sequences consisting essentially of

5'-CTGCCCTACTTGATTGATGGG-3' and

5'-CTGGATTGTAGCAGATCATGC-3';

(c) amplifying the DNA by subjecting the mixture to alternating cycles of temperatures which allow denaturation, annealing and DNA synthesis; and
   (d) determining whether a product is obtained from amplifying the DNA.

2. A method according to claim 1, wherein the tissue sample is a highly necrotic tumor tissue sample.

* * * * *